US008440447B2

(12) United States Patent
Stone et al.

(10) Patent No.: US 8,440,447 B2
(45) Date of Patent: May 14, 2013

(54) EXTRACTION AND CONCENTRATION METHOD

(75) Inventors: Henry Stone, Colbert, GA (US); Cam Greene, Jefferson, GA (US); Peter Holt, Colbert, GA (US); Richard Gast, Watkinsville, GA (US); Kunho Seo, Gaithersburg, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 2017 days.

(21) Appl. No.: 11/445,091

(22) Filed: May 31, 2006

(65) Prior Publication Data

US 2006/0216703 A1    Sep. 28, 2006

Related U.S. Application Data

(63) Continuation of application No. 10/225,419, filed on Aug. 22, 2002, now abandoned.

(51) Int. Cl.
*C12N 7/02* (2006.01)
*C12Q 1/70* (2006.01)

(52) U.S. Cl.
USPC .............................................. 435/239; 435/5

(58) Field of Classification Search .................. None
See application file for complete search history.

(56) References Cited

U.S. PATENT DOCUMENTS

| 4,140,753 A | * | 2/1979 | Edgington et al. ............ 436/542 |
| 5,367,054 A | * | 11/1994 | Lee ............................... 530/359 |
| 5,932,250 A | | 8/1999 | Stolle et al. |

OTHER PUBLICATIONS

R. K. Gast et al., "Serologic Detection of Experimental *Salmonella enteritidis* Infections in Laying Hens by Fluorescence Polarization and Enzyme Immunoassay", *Avian Diseases*, vol. 46, pp. 137-142, 2002.
R. K. Gast et al., "Research Note: Detection of *Salmonella* Serogroup D-Specific Antibodies in the Yolks of Eggs Laid by Hens Infected with *Salmonella enteritidis*", *Poultry Science*, vol. 70, pp. 1273-1276, 1991.
R. K. Gast et al., "Serological Detection of Experimental *Salmonella enteritidis* Infections in Laying Hens by Fluorescence Polarization and Enzyme Immunoassay", *Poultry Science*, vol. 80, pp. 1044, 2001.
D. N. Phalen et al., "Failure of Maternally Derived Yolk IgG to Reach Detectable Concentrations in the Sera of Nestling Budgerigars (*Melopsittacus undulatus*)", *Avian Diseases*, vol. 39, pp. 700-708, 1995.
par Nöelle Dupuy et al., "Influence de différents traitements du jaune d'oeuf sur le titrage des anticorps vitellins dirigés contre quatre virus aviaires par la technique ELISA", *Rec. Méd. Vét.*, vol. 170, (12), p. 847-855, 1984. (abstract only).
T. H. Piela et al., "Use of Egg Yolk in Serological Tests (ELISA and HI) to Detect Antibody to Newcastle Disease, Infectious Bronchitis, and *Mycoplasma gallisepticum*", *Avian Diseases*, vol. 29, (4), pp. 877-883, Jan. 1984.
L. D. Keck et al., "Antibody Detection in Matched Chicken Sera and Egg-Yolk Samples by Commercial Enzyme-Linked Immunosorbent Assay Kits for Newcastle Disease Virus, Infectious Bronchitis Virus, Infectious Bursal Disease Virus, and Avian Reovirus", *Avian Diseases*, vol. 37, pp. 825-828, 1993.
T. Deignan et al., "Comparative Analysis of Methods of Purification of Egg Yolk Immunoglobulin", *Food and Agricultural Immunology*, vol. 12, pp. 77-85, 2000.
J. Brown et al., "The Relationship of Egg Yolk and Serum Antibody. I. Infectious Bursal Disease Virus", *Avian Diseases*, vol. 33, pp. 654-656, 1989.
R. K. Gast et al., "Applying Tests for Specific Yolk Antibodies to Predict Contamination by *Salmonella enteritidis* in Eggs from Experimentally Infected Laying Hens", *Avian Diseases*, vol. 41, pp. 195-202, 1997.
R. K. Gast et al., "Assessing the Sensitivity of Egg Yolk Antibody Testing for Detecting *Salmonella enteritidis* Infections in Laying Hens", *Poultry Science*, vol. 76, pp. 798-801, 1997.
E. M. Akita et al., "Immunoglobulins from Egg Yolk: Isolation and Purification", *Journal of Food Science*, vol. 57, (3), pp. 629-634, 1992.
C. R. Greene et al., "An improved chromatographic method for the separation of egg yolk IgG into subpopulations utilizing immobilized metal ion ($Fe^{3+}$) affinity chromatography", *Journal of Immunological Methods*, vol. 209, pp. 155-164, 1997.
A. Silim et al., "Comparison of Egg-Yolk and Serum Antibody Titers to Four Avian Viruses by Enzyme-Linked Immunosorbent Assay Using Paired Field Samples", *Avian Diseases*, vol. 33, pp. 643-648, 1989.
R. D. McLaren et al., "The use of caprylic acid for the extraction of the immunoglobulin fraction from egg yolk of chickens immunised with ovine α-lactalbumin", *Journal of Immunological Methods*, vol. 177, pp. 175-184, 1994.

* cited by examiner

*Primary Examiner* — Stacy B. Chen
(74) *Attorney, Agent, or Firm* — Howard V. Owens; Lesley Shaw; John D. Fado

(57) ABSTRACT

A method for extraction and concentration of antibodies, antigens, bacteria and virus from biological samples. The method also provides a preparation that is suitable for use as a vaccine. The method includes the addition of liquid carboxylic acids and a centrifugation step.

10 Claims, 4 Drawing Sheets

EXTRACTION AND CONCENTRATION METHOD

This is a continuation of application Ser. No. 10/225,419, filed Aug. 22, 2002, now abandoned, which is herein incorporated by reference in its entirety.

BACKGROUND OF THE INVENTION

1. Field of the Invention

This invention relates to methods for extraction and concentration of water and oil soluble compounds from a biological sample using liquid carboxylic acids.

2. Description of the Related Art

*Salmonella* serotype *enteritidis* (SE) emerged as a major cause of human salmonellosis in the United States throughout the 1980s and 1990s. Of the 360 SE outbreaks with a confirmed source, 279 (82%)) were associated with raw or undercooked shell eggs between 1985 and 1998 (CDC, 2000). Grade-A shell eggs have been attributed to the human salmonellosis problem due to the ability of SE to infect ovarian tissues and to be deposited into the developing egg. It is difficult to detect flocks or individual birds that may be infected with SE and lay contaminated eggs since laying hens seldom show any clinical symptom of SE infection. Studies indicate that the percentage of infected eggs is extremely low and sporadic with most contaminated eggs having small number of SE (Humphrey, 1994). Culturing both environmental samples and bird tissues does not prove the birds are laying SE infected eggs. The only method of directly proving that a flock is laying SE-contaminated eggs is by culturing the organism from eggs.

Conventional methods for detection of *Salmonella* from eggs take 5-7 days and are labor-intensive, involving isolation of the organism using pre-enrichment as well as selective enrichment procedures and serological confirmation tests. Detection of small numbers of SE in inoculated pools of egg contents was successful using direct plating of incubated egg pools onto agar plates although the more enrichments steps applied, the better the sensitivity achieved (Gast, Poultry Science, 72, 1611-1614, 1993). Supplementing pools of egg contents with iron in the form of ferrous sulphate and concentrated enrichment broth has been suggested to improve detection of SE from raw eggs without using enrichment broth (Gast and Beard, Poultry Sci., Volume 70, 1273-1276 1991; Cudjoe et al., Int. J. Food Microbiology, Volume 23, 149-158, 1994; Gast and Holt, Jour. Food Prot., Volume 61, 107-109, 1998). More rapid methodologies have been developed using ELISA and PCR techniques (Holt et al., J. Food Prot., Volume 58, 967-972, 1995; Woodward and Kirwan, Vet. Rec., Volume 138, 411-413, 1996). In contrast to conventional methods, these tests can detect SE in two days. However, they are not free of drawbacks. The tests involve time-consuming enrichment incubations, exhibit varying degrees of cross-reactions, and both systems have been known to produce false positive reactions. The sensitivity of rapid detection methods for SE in eggs was substantially decreased due to interference of egg contents (Brigmon et al., Poultry Science, Volume 74, 1232-1236, 1995). Cudjoe et al. (1994, supra) found that the more viscous, undiluted mixtures of eggs showed the highest particle loss compared with diluted samples when immunomagnetic beads were applied to recover SE from raw eggs.

U.S. Pat. No. 5,367,054 (Young-Zoon, Nov. 22, 1994) discloses methods for isolating and purifying immunoglobulins from eggs which includes a first step of extracting a diluted, homogenized egg yolk with a composition containing one or more medium-chain fatty acids, i.e. any fatty acid having 6-12 carbon atoms, such as caprylic acid, caproic acid, capric acid, and lauric acid while homogenizing the mixture for a second time.

U.S. Pat. No. 5,932,250 (Stolle et al., Aug. 3, 1999) discloses extraction of egg yolk IgY protein fraction using caprylic acid where egg yolk is diluted 7.5 fold with deionized water and then diluted 1:1 with 0.06 M acetate buffer, pH 5. One percent caprylic acid is blended in and the mixture allowed to stand for 2 hours for separation of the aqueous (bottom) layer and the oil solubles (top layer); with immunoglobulin in the aqueous layer. The bottom layer is neutralized and diafiltered and concentrated.

McLaren et al. (Journal of Immunological Methods, Volume 177, 175-184, 1994) disclose extraction of a diluted pool of egg yolk with a final caprylic acid concentration of 6% (v/v). After the addition of caprylic acid, the mixture was stirred for two hours at room temperature followed by centrifugation to obtain a supernatant containing immunoglobulin.

While various methods have been disclosed for obtaining proteins, such as immunoglobulins, from biological samples, such as egg yolk, there remains a need in the art for methods for rapid extraction of proteins, such as immunoglobulins and antigens; and infectious agents such as bacteria, from biological samples. The present invention provides a method for extracting such proteins and/or infectious agents from biological samples which is fast, provides a concentrated sample, provides increased sensitivity when used in diagnostic testing, and is different from prior art methods and solves some of the problems associated with prior art extraction methods.

SUMMARY OF THE INVENTION

It is therefore an object of the present invention to provide a method for producing a biological sample for diagnostic testing which includes a step of extracting a biological sample with a medium chain carboxylic acid or mixture of carboxylic acids to obtain an aqueous concentrated sample.

Another object of the present invention is to provide an extracted, concentrated sample from a biological material for use in a diagnostic test.

A still further object of the present invention is to provide an extracted, concentrated, and sterile sample from a biological sample for use as a vaccine to confer immunity.

Another object of the present invention is to provide a method for concentrating antibodies or antigens in a biological sample for diagnostic testing wherein a biological sample is extracted with a medium chain carboxylic acid or a carboxylic acid with a carbon number higher than 18 which is a liquid and does not damage the material to be extracted and concentrated.

A further object of the present invention is to provide a method for preparing a test sample from an animal egg that includes extracting whole egg, egg yolk, or egg albumin with a medium chain carboxylic acid or a carboxylic acid with a carbon number higher than 18 which is a liquid and does not damage the material to be extracted and concentrated to form an aqueous sample for diagnostic testing.

Further objects and advantages of the invention will become apparent from the following description.

BRIEF DESCRIPTION OF THE DRAWINGS

FIG. 1 is a photograph of an extracted egg yolk sample after centrifugation showing the layers containing oily solubles, ester products, and antibody and aqueous solubles.

DETAILED DESCRIPTION OF THE INVENTION

The present invention provides a method for extracting and concentrating proteins, such as antigen and antibody; and infectious agents such as bacteria and virus, from a biological material, such as egg contents, which increases the sensitivity of tests for rapid detection and provides an inexpensive method for preparing samples for testing for proteins, such as, for example, immunoglobulins, antigens, and infectious agents such as and without limitation thereto, *Salmonella*, Newcastle disease, avian leukosis, infectious bursal disease, adenovirus disease, reovirus, pox, laryngotracheitis, avian influenza, Marek's disease, etc. Diagnostic tests include tests such as hemagglutination-inhibition (HI) tests, microagglutination tests (MA), plate agglutination, gel precipitin tests, strip chromatography, ELISA, etc.; or tests based on passing a sample through a beam of light such as spectrophotometry, fluorescence polarization, etc.

The term "immunoglobulin or "fragment thereof" is intended to mean antibody, especially antibody that is deposited into eggs of avian, reptile, amphibian, or fish during oogenesis. There are three classes of immunoglobulins deposited in eggs, IgY, IgA, and IgM. Biologically active fragments of these immunoglobulins are well recognized in the art and include, for example, Fab fragment (having antigen binding site), Fc fragment (the protein domain involved in immune regulation [the fragment that crystallizes]), and the Fc' fragment.

Medium chain saturated or unsaturated carboxylic acids, specifically fatty acids, including straight chain and branched, having at least six carbon atoms and up to and including eighteen carbon atoms such as, for example, caprylic acid, capric acid, oleic acid, isostearic acid, caproic acid, and mixtures thereof. Furthermore any acids of carbon numbers higher than 18 that are liquid and do not damage the extracted and concentrated sample, such as protein, bacteria, and virus, are useful.

The term immune egg is intended to mean eggs from any egg-producing members of the avian, reptile, amphibian, or fish family which have been immunized.

Avian includes, but is not limited to, poultry and fowl, such as chickens, turkeys, geese, ducks, pheasant, emu, ostrich, etc.

Reptile includes, but is not limited to, Crocodilia such as alligators, caiman, crocodiles, and garivals, etc.; Chelonia such as tortoises and turtles; Squamata such as lizards and snakes, and Rhynchocephalia such as tuatara.

Amphibians include, but are not limited to, frogs, toads, and salamanders.

Figure 1:
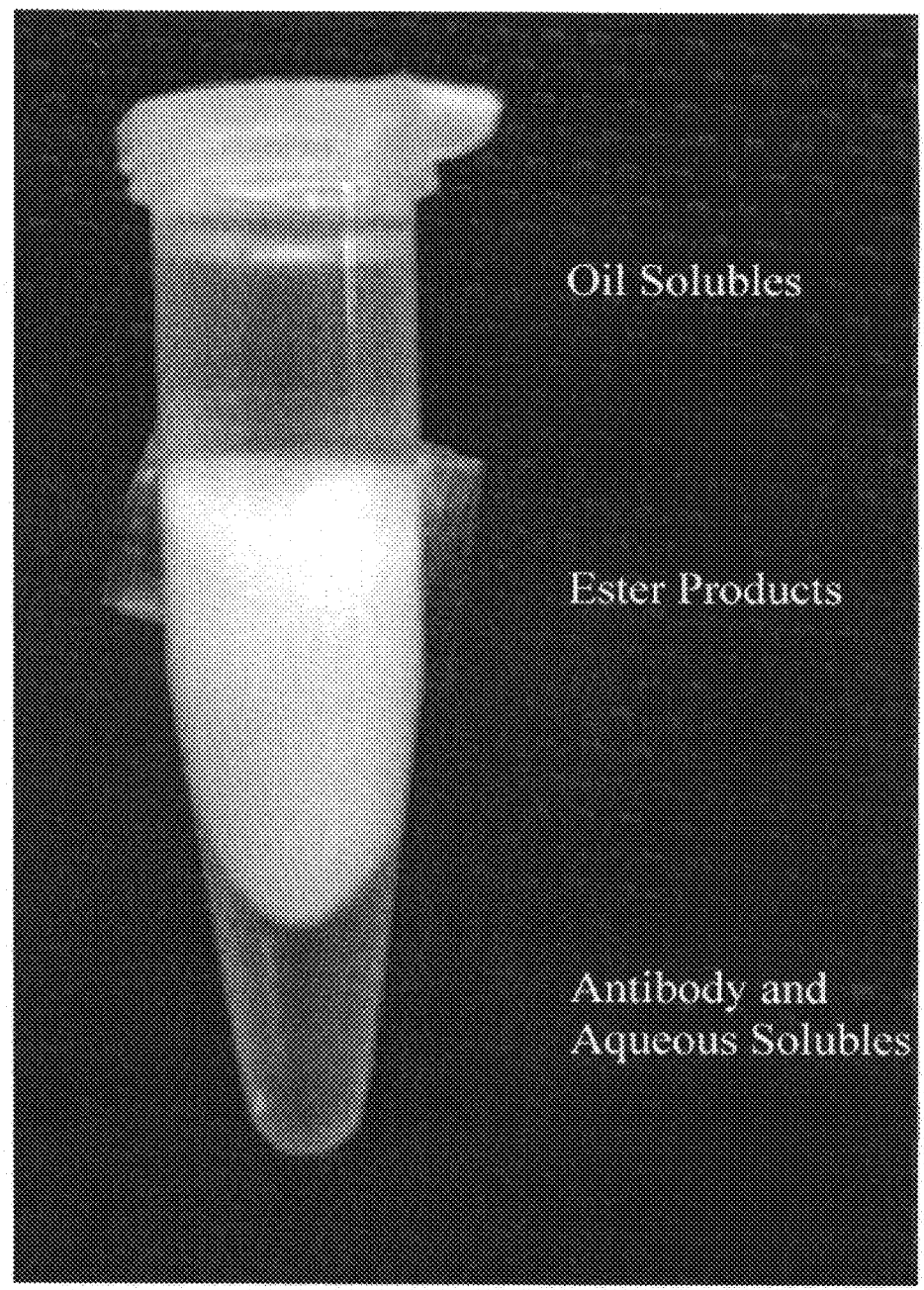
Figure 2:
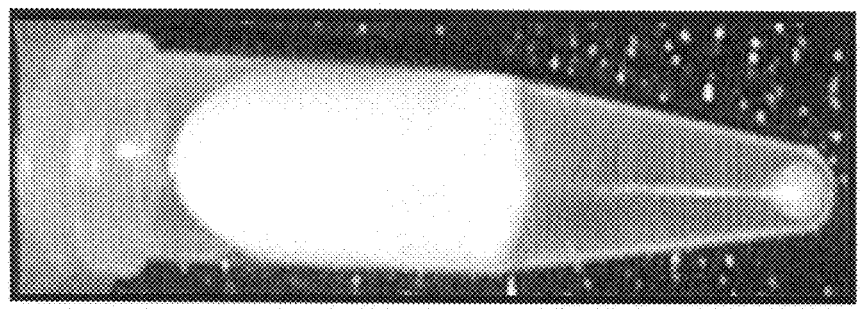
FIG. 2 is a photograph of extracted whole egg containing albumin, yolk, and *Salmonella enteritidis* showing the layers containing oily solubles, solid reaction products, aqueous solubles, and bacterial pellet.
Figure 3:
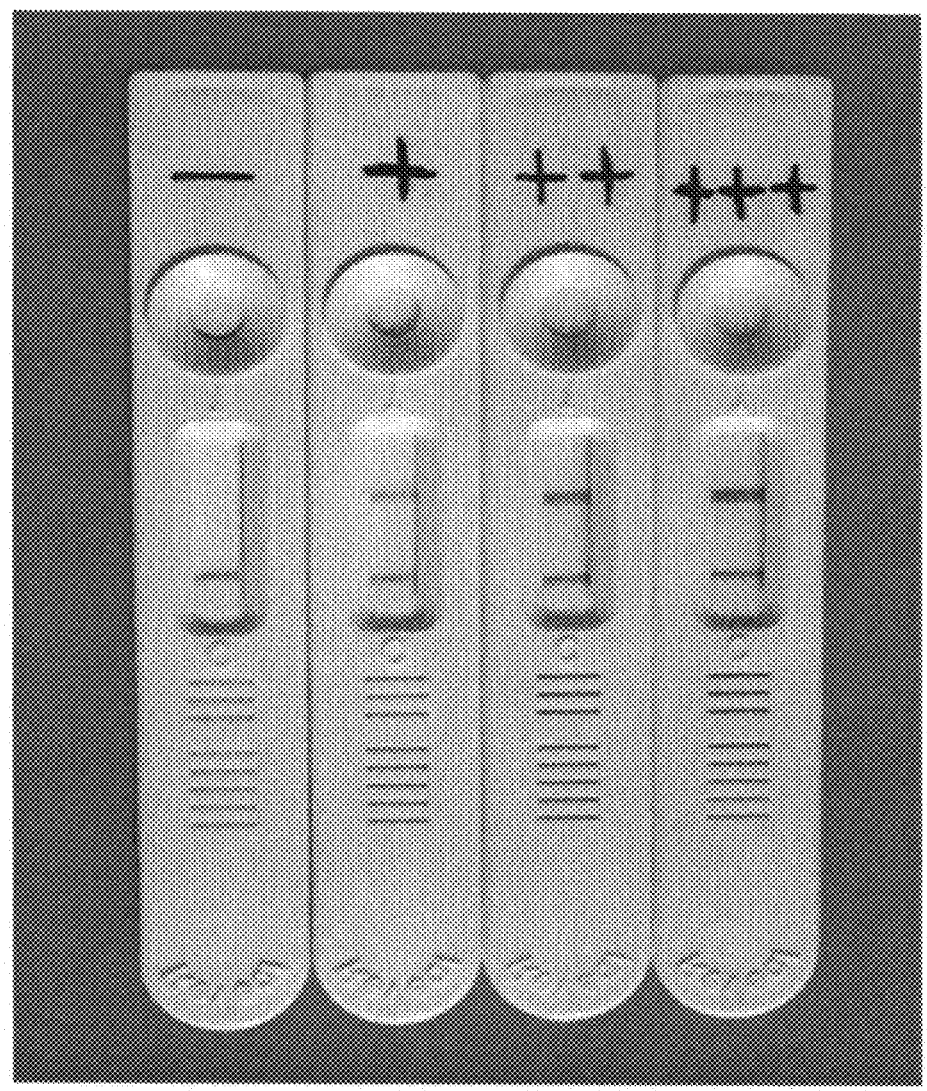
FIG. 3 is a photograph of lateral REVEAL™ *Salmonella enteritidis* flow test panels (Neogen Co., Lansing Mich.) showing a scale of band intensities in a test panel kit with a control and egg yolk extracts containing increasing amounts of *Salmonella enteritidis*.

The method of the present invention extracts and concentrates proteins such as antibodies, antigens; and bacteria or viruses, such as *Salmonella enteritidis*, for example, in an aqueous medium to provide samples for use in conventional or automated assays. The method provides clear, particle free samples (See FIGS. 1 and 2) that can be applied to conventional serological tests and used in methods where measurements are based on beams of light. The method is fast, employing a mixing step and a centrifugation step. The method removes organisms such as *Salmonella enteritidis* from samples to provide a preparation that is suitable for use as a vaccine, in some instances such as with *Salmonella enteritidis*, the preparation should be sterile (FIG. 2). Samples can be pooled which saves time and increases scanning range. The extracted samples can be further processed for concentration by precipitation methods to increase sensitivity. Bulk extraction and concentration is also an option. The method provides samples that can be used directly or with minimal processing on chromatographic columns to detect subgroups of antibody and their amounts.

Extraction of antibody from egg yolks or blended whole egg contents for assay of specific antibody against disease is one application of the present invention. Eggs are a quick source of antibodies and their collection does not interfere with egg lay or involve contact with the animal as does bleeding for serum testing. The method is also applied for detection of antigen to determine infection by a pathogen. Furthermore, oil emulsion vaccines can be separated into oil and aqueous phase to determine antigen amount and its relevance to potency before purchase. The extract can also be used for antibody recovery and purification in high yield since the antibody extract only requires two steps from egg yolk and only requires a dialysis step and one pass through a thiophilic chromatography column. Furthermore, the extracts are sterile and can be injected into embryos to establish early protection in hatched chicks using the low viscosity soluble egg components compatible for embryos.

The method of the present invention includes extracting a biological sample such as whole egg, egg yolk, egg albumin, bacteria in growth mediums, and infected tissues, for example, with a medium chain saturated or unsaturated carboxylic acid, such as for example, any carboxylic acid that is a liquid near or at room temperature, caprylic acid, capric acid, oleic acid, isostearic acid, or mixtures thereof or with at least one carboxylic acid with a carbon number higher than 18 which is a liquid and does not damage the material to be extracted and concentrated. Ratios of organic acid and samples are used that provide maximum yield of soluble product and that provide a viscosity that will allow a thorough mixing. Some ratios, 1:1 for example, will result in a viscous admix since the esters formed are surfactants and will emulsify the aqueous product causing the generation of new surfaces which results in friction (viscosity). Addition of oily acid or sample will lower viscosity in samples that emulsify. Very strong mixing should be avoided since this may generate strong water-in-oil emulsions and the aqueous product can not be centrifuged out of these. A ratio of about two parts biological sample to about 1 part acid (v:v or w:w) is preferred for most mixtures used in small (approximately $\leq$2 ml) centrifuge tubes. The sample with acid is mixed until the sample is viscous, at least about 1 minute, using any conventional means for mixing such as, for example, stirring, vortexing, blending, mechanical or manual shaking, etc. Blenders and emulsifying machines should be used at low speed to prevent forming an emulsion. The sample is then centrifuged for about 5 to 10 minutes at about 10,000×g to about 16,000×g. For bacterial and viral component recovery, the sample is centrifuged at about 16,000×g or higher to pellet antigens or about 1000×g to about 10,000×g to suspend antigen. One of ordinary skill in the art could readily determine centrifuge speed based on the density of the antigen in the sample. The bottom aqueous layer is sampled for assay using any conventional means for sampling such as, for example, syringe, pipet, cutting bottom of tube, etc.

The following examples are intended to further illustrate the invention and are not intended to limit the scope of the invention which is defined by the claims. Chicken eggs are used as a model system for the present invention.

Example 1

Single-comb white leghorn hens, 26-32 weeks old, from the USDA-Agricultural Research Service Southeast Poultry Research Laboratory (Athens, Ga.) specific-pathogen-free flock (SPF) were reared in disease containment buildings with appropriate diet and husbandry. They were housed in individual laying cages and grouped in separate rooms for different treatments. They were fed water and feed ad libitum.

One ml of blood was drawn from the wing vein for serum collection immediately before challenge of hens and at weekly intervals.

Eggs were collected daily and identified individually for each hen. Egg yolks were separated from the albumin by cracking the egg, dropping most of the albumin and rolling the intact yolk over into a 50 ml centrifuge tube. Residual albumin was removed with a syringe when the yolk was at the lip of the tube. The whole yolk was mixed to assure even antibody distribution before sampling.

For whole egg contents, eggs were cracked and the contents emptied into a narrow neck 250 ml blender cup (Waring blender, Dynamics Corp. of America, New Hartford, Conn.). They were blended at the low setting with on-off switching, as needed, to prevent formation of a vortex which forms bubbles and ultra fine particles that interfere with the fluorescence polarization (FP) assay. This process usually takes about 4 seconds or less.

For extraction of yolk and whole egg contents, about a one ml sample and about a 0.5 ml sample of a mixture of 2 parts oleic acid and 1 part caprylic acid were mixed with an applicator stick in a 1.7 ml Eppendorf centrifuge tube for about 2 minutes or until the mixture became viscous. The tube is then centrifuged at about 14,000×g for about ten minutes. The clear solution at the bottom of the tube (about 0.2 ml for yolk and about 0.5 ml for whole egg contents) was then sampled (about 20 µl unchanged or undiluted in about 1 ml of phosphate buffered saline (PBS)) for the FP assay. The acids react with the active hydrogens in the sample forming water which solubilized the antibody. This soluble antibody was used for assay.

For the fluorescence assay, instrumentation and fluorescence antigen (tracer) was developed by Diachemix Corp. (Grayslake, Ill.). One disposable 10×75 mm glass tube (Fisher Scientific, Pittsburgh, Pa.) containing about 1 ml of phosphate buffered saline (PBS) is required for each assay. The instrumentation is equilibrated one time for temperature and antigen spin in one ml of PBS for a baseline value. For antibody testing, about 20 µl of each sample is mixed in about 1 ml of PBS per tube and equilibrated (blanked) on the machine for a baseline. Then the tube is removed and about 10 µl of tracer (fluorescent antigen) is admixed gently. The tube is replaced and the polarized beam of the machine is allowed to sweep the sample 25 times to reach an endpoint value. Each antibody determination takes less than three minutes. Samples (PBS and sample) can be mixed ahead of time before the tracer is added. FP positive values are those two standard deviations above the mean FP values for the negative control samples.

Two experiments, each with two replicate trials were done. Experiment one tested serum and yolk samples while experiment two tested whole egg contents. Trial one of experiment one used 26 week old hens, six uninoculated controls and three groups of ten receiving about a 1 ml oral administration into the crop containing about $10^6$ colony forming units (CFU) of a phage type 13a strain of *Salmonella enteritidis*, about $10^8$ CFU of the same strain, or about $1.2 \times 10^8$ CFU of *Salmonella typhimurium*. *Salmonella* strains were regenerated from frozen stocks by 37° C. incubation in tryptone soya broth (Oxoid USA, Ogdensburg, N.Y.) overnight. Cell density was adjusted to about a 1 ml dose in the broth.

For trial two of experiment one, the same treatments were given to about 32 week old hens.

The eggs from trial one were collected, as described above, and the contents of one egg from each individual hen at about 22-24 days post challenge were blended and tested for antibodies in the extraction or untreated supernatants obtained by centrifugation (about 14,000×g for about 10 minutes) or untreated supernatants obtained from overnight settling. The three samples were tested by FP, microagglutination (MA), Pullorum test (PT) where possible, or gel precipitation (AGPT) for antibodies against *Salmonella enteritidis*.

Eggs from trial two were pooled (2-5 eggs) from individual hens through the $4^{th}$ week after challenge and their contents blended. The pools were tested by FP only. Samples of the pools tested were extracted with the acid mixture as described above.

The results of trials one and two are shown below in Tables 1 and 2, respectively. Hens of the non-infected control groups were negative for *Salmonella enteritidis* by all tests of both trails. The $10^6$ CFU groups of both trial were serologically positive by FP from about 66.7 to about 80 percent over 14 to 35 days post infection. Yolks of these hens were SE antibody positive by FP from about 37.5 to about 100%. The PT, MA and AGPT tests all indicated about 83.3% positive at about 35 days post infection. In both trials of *Salmonella typhimurium* infected hens FP disclosed a range of about 30 to 60% positives in the sera. In the yolks the range was about 30-90%. For the PT, MA, and AGPT tests at about 35 days post infection, the positives were about 28.6%, 42.9% and 14.3%, respectively.

In experiment two, hatchmate hens in separate disease containment rooms were challenged with *Salmonella enteritidis* by either the oral, intravenous (IV) or aerosol route. Aerosol challenge was delivered by spraying in the face with about a 10 ml volume containing about $10^9$ CFU. IV challenge was with about a 0.5 ml dose of about $10^7$ or about $10^5$ CFU into the wing vein. Oral challenge was by gavage of about a 1 ml volume into the crop. The samples were collected as described above for experiment one.

For experiment 2, trial 1, egg samples of all non-infected hens were negative by all applicable tests. The egg samples of the IV infected group were all positive in all sample treatment groups by all tests. In the aerosol infected groups FP detected the most positives with about 93.3%, 73.3%, and 73.3% for the extracts, supernatants from centrifugation, and from settling, respectively. Positives by FP in the orally infected group were about 61.1%, 88.9%, and 61.1% for corresponding treatment groups. With the exception of the PT on the extract of the orally infected group (about 88.9%) values from the conventional tests ranged from about 0% to about 60% for aerosol and oral groups (Table 3 below).

In trial 2, samples of the nonimmune groups were negative for the blended only group. The extract and centrifuged supernatant control groups showed about 6.25% positives. The IV challenged groups were 100% positive. Positives for the extracts and blended only samples were the same at about 83.3% and 85.7% for aerosol and oral challenges. Among the supernatant samples, positives were about 66.7% for aerosol and about 64.3% for oral challenges (Table 4 below).

TABLE 1

Percent positives detected by Fluorescence polarization in serum and yolk extracts.

| | Days Post Infection | | |
|---|---|---|---|
| | 14 | 21 | 28 |
| Controls | | | |
| serum | 00.0 | 00.0 | 00.0 |
| yolk | 00.0 | 00.0 | 00.0 |
| $10^6$ CFU | | | |
| serum | 77.8 | 66.7 | 77.8 |
| yolk | 66.7 | 55.6 | 100.0 |
| $10^8$ CFU | | | |
| serum | 100.0 | 100.0 | 100.0 |
| yolk | 100.0 | 86.7 | 100.0 |
| $10^8$ CFU | | | |
| [A]ST | | | |
| serum | 40.0 | 50.0 | 30.0 |
| yolk | — | 30.0 | 90.0 |

[A]ST = *Salmonella typhimurium*

TABLE 2

Percent Positives detected by Fluorescence polarization in serum and yolk extracts.

| | Days Post Infection | | |
|---|---|---|---|
| | 21 | 28 | 35 |
| Controls | | | |
| serum | 00.0 | 00.0 | 00.0 |
| yolk | 00.0 | 00.0 | 00.0 |
| [A]yolk PT | — | — | 00.0 |
| [B]yolk MA | — | — | 00.0 |
| [C]yolk AGPT | — | — | 00.0 |
| $10^6$ CFU | | | |
| serum | 80.0 | 77.8 | 77.8 |
| yolk | 37.5 | 87.5 | 66.7 |
| [A]yolk PT | — | — | 83.3 |
| [B]yolk MA | — | — | 83.3 |
| [C]yolk AGPT | — | — | 83.0 |
| $10^8$ CFU | | | |
| serum | 90.0 | 80.0 | 90.0 |
| yolk | 85.7 | 100.0 | 100.0 |
| [A]yolk PT | — | — | 90.0 |
| [B]yolk MA | — | — | 80.0 |
| [C]yolk AGPT | — | — | 90.0 |
| $10^8$ CFU | | | |
| [D]ST | | | |
| serum | 60.0 | 30.0 | 67.7 |
| yolk | 00.0 | 67.7 | 42.9 |
| [A]yolk PT | — | — | 28.6 |
| [B]yolk MA | — | — | 42.9 |
| [C]yolk AGPT | — | — | 14.3 |

[A]PT = Pullorum test;
[B]MA = microagglutination test;
[C]AGPT = agar gel precipitin test;
[D]ST = *Salmonella typhimurium*

TABLE 3

Percent positives detected 24 days post infection in blended whole egg contents by fluorescence polarization and conventional tests.

| | Route of Infection | | |
|---|---|---|---|
| Sample treatment | Aerosol | Intravenous | Oral |
| Acid Extracts | | | |
| FP | 93.3 | 100.0 | 61.1 |
| Control | 00.0 | 00.0 | 00.0 |
| MA | 13.3 | 100.0 | 44.4 |
| Control | 00.0 | 00.0 | 00.0 |
| PT | 60.0 | 100.0 | 88.9 |
| Control | 00.0 | 00.0 | 00.0 |
| AGPT | 20.0 | 100.0 | 33.3 |
| Centrif. Sup. | | | |
| FP | 73.3 | 100.0 | 88.9 |
| Control | 00.0 | 00.0 | 00.0 |
| MA | 06.7 | 100.0 | 22.2 |
| Control | 00.0 | 00.0 | 00.0 |
| PT | NA | NA | NA |
| AGPT | 00.0 | 100.0 | 11.1 |
| Control | 00.0 | 00.0 | 00.0 |
| Settling Sup. | | | |
| FP | 73.3 | 100.0 | 61.1 |
| Control | 00.0 | 00.0 | 00.0 |
| MA | 00.0 | 100.0 | 16.7 |
| Control | 00.0 | 00.0 | 00.0 |
| PT | NA | NA | NA |
| AGPT | 00.0 | 100.0 | 11.1 |
| Control | 00.0 | 00.0 | 00.0 |

MA = microagglutination test;
PT = Pullorum test;
AGPT = agar gel precipitin test

TABLE 4

Percent positives detected by fluorescence polarization in individual blended whole egg pools of hens infected by different routes. Four Weeks post infection.

| | Route of Infection | | |
|---|---|---|---|
| Sample Treatment | Aerosol | Intravenous | Oral |
| Acid Extracts | 83.3 | 100.0 | 85.7 |
| Control | 06.25 | 06.25 | 06.25 |
| Centrif. Sup | 66.7 | 100.0 | 64.3 |
| Control | 06.25 | 06.25 | 06.25 |
| Blended only | 83.3 | 100.0 | 85.7 |
| Control | 00.0 | 00.0 | 00.0 |

Example 2

This example demonstrates the use of fatty acid extraction of the present invention to detect the presence of *Salmonella* in eggs. *Salmonella enteritidis* (SE) was obtained from stocks kept at the Southeast Poultry Research Laboratory (SEPRL, Athens, Ga.). SE was selected for resistance to rifampicin (Seo et al., J. Food Prot., Volume 63, 545-548, 2000). Purity of the cultures was confirmed using serotyping (Difco Laboratories, Detroit, Mich.). Cultures were grown in tryptic soy broth (TSB; Difco) and viable counts were obtained by plating 10-fold serial dilutions of broth cultures on nutrient agar (Difco) and incubating plates at 37° C. overnight. Whenever necessary, cultures were diluted in phosphate buffered saline (PBS, pH 7.2) as needed and counts were made as above.

A lateral flow panel test (Neogen Co., REVEAL™ *Salmonella enteritidis*, Lansing, Mich.) (FIG. 1) was used to determine the presence of *Salmonella* in about a 100 µl portion of a sample that was placed into the round sample port of the test device. The test panel is based on chromatography. This initiated lateral flow through a reagent zone containing specific anti-*Salmonella enteritidis* antibodies conjugated to colloidal gold particles. The antibody used in the device was developed at the SEPRL and disclosed in a previous study (Holt et al., J. Food Prot., Volume 58, 967-972, 1995). Test results were interpreted as positive or negative, scored on a scale from 0 to 4, after 20 minutes from the addition of the sample culture (FIG. 1).

In order to test the detection limit of the assay, pure cultures of SE were grown in TSB and tested at concentrations between $10^0$ to $10^8$ cells/ml.

To determine the minimum number of SE needed for generating a positive result, eggs were spiked with a known number of SE. Eggs were collected from the SEPRL specific-pathogen-free flock and were soaked in about 70% alcohol to disinfect the shells before they were broken. The egg contents were pooled and homogenized for about 1 minute in a Stomacher. About 10 mls of egg contents were allocated into 15 ml test tubes and mixed with about 100 µl of different 10-fold SE dilutions to generate samples with known number or organisms. For negative controls, about 100 µl of PBS was mixed with about 10 ml of egg contents.

In order to enhance the ability to detect SE, egg contents were either diluted with PBS, extracted with a mixture of oleic and caprylic acid, or enriched by culturing in broth for about 24 hours at 37° C. For dilution, egg contents with different numbers of SE were diluted with PBS at about 1:2, 1:4, and 1:10 and about 100 µl of each sample was adsorbed to a test panel to find the optimum running ability of the sample and detection limit.

For extraction, one ml of whole egg with various concentrations of SE and 0.5 ml of a mixture of about 2 parts oleic acid and one part caprylic acid were stirred together with an applicator stick in a 1.7 ml Eppendorf centrifuge tube to allow the acid to react and form an ester with reactive hydroxyl groups. The reaction forms water as a by-product and at the same time breaks up the structure of the egg contents which releases the bacteria and aqueous solubles. The reaction is near completion when the mixture becomes viscous, in approximately 1-2 minutes at room temperature. The tube is then centrifuged for about 5 minutes at about 10,000×g in an Eppendorf tabletop centrifuge. Centrifugation forms an oily layer with yellow carotenes and oil solubles on the top, a soapy hard layer of esters in the middle, and a clear aqueous layer with bacteria and soluble protein on the bottom (FIG. 2). The aqueous layer which contains antigen and bacteria was removed with a 1 ml syringe and about 100 µl of the solution was applied to a test panel.

For enrichment, each homogenized egg sample containing a known SE concentration was mixed with TSB at various ratios between egg contents and enrichment broth. After about a 24 hour incubation at about 37° C., about 100 µl of each broth culture was adsorbed onto a test panel and the results were determined after about 20 minutes.

The minimum concentration of SE to generate a positive band on the test panel was approximately $10^7$ cells/ml in pure culture and no cross-reactivity was detected with other *salmonella* serovars. One variable which is crucial for the success of the test panel is the ability of the sample to be effectively wicked down the membrane so that the organism or antigen present in the sample can interact with the detection antibodies. Whole egg does not effectively transit the panel due to the viscous nature of the sample (Table 5 below). Progressively diluting the egg with PBS reduces the viscosity of egg contents and allows the more effective wicking of sample. About a 1:10 dilution of sample with PBS works best. However, the intensity of the positive band appeared weaker as the dilution was increased resulting in low sensitivity to about $10^8$ cells/ml. Similar drawbacks of immunoassays were reported in a previous study (Brigmon et al., 1995; supra) when they used ELISA to detect SE in eggs. The sensitivity of the ELISA system was decreased to $10^7$ cells/ml when SE was mixed with 10% homogenized whole eggs while SE was detected at a minimum concentration of $10^4$ cells/ml in pure culture. This suggests that the albumin and lipids in yolk may act as blocking agents inhibiting antibody binding in the ELISA. Extraction of bacterial antigen out of egg contents using fatty acid provided excellent running capability and stronger positive signal on the test panel kit without sacrificing the sensitivity. The detection limit of the test kit increased to about $10^6$ cells/ml in whole egg contents using fatty acid extraction (Table 6). Egg pools inoculated with 1-5 cells/ml of SE were detected as SE-positive after 24 hours incubation at 37° C. when the direct antigen extraction method was used with the test panel (Table 7). This technique could lead to relatively rapid and inexpensive detection of SE in whole eggs by saving enrichment media and reducing incubation time.

TABLE 5

Direct detection of SE from whole egg contents using dilution technique with PBS and antigen extraction with a fatty acid mixture.

| | Whole egg | Egg:PBS (1:2) | Egg:PBS (1:4) | Egg:PBS (1:10) | Egg:acid (2:1) |
|---|---|---|---|---|---|
| Band intensity | $-^A$ | ++ | ++ | + | +++ |
| Sample Running | poor | not good | good | very good | very good |
| Controls | — | — | — | — | — |

$^A$ = darkness of the band = negative test

TABLE 6

Detection limit of direct detection of SE from whole egg contents using dilution technique with PBS and antigen extraction with fatty acid mixture.

| | METHODS | |
|---|---|---|
| Number of cells (CFU/ml) | Dilution Technique | Fatty Acid Extraction |
| $10^8$ | +++ | +++ |
| $10^7$ | + | +++ |
| $10^6$ | − | ++ |
| $10^5$ | − | −+ |

TABLE 7

Direct detection of SE from whole egg contents using dilution technique with PBS and antigen extraction with fatty acid mixture.

| | Methods | |
|---|---|---|
| Samples | Dilution Technique | Fatty Acid Mixture Extraction |
| Negative Control | −(3/3) | −(3/3) |
| Inoculated Eggs | +(10/10) | +++(10/10) |

Example 3

Figure 4:
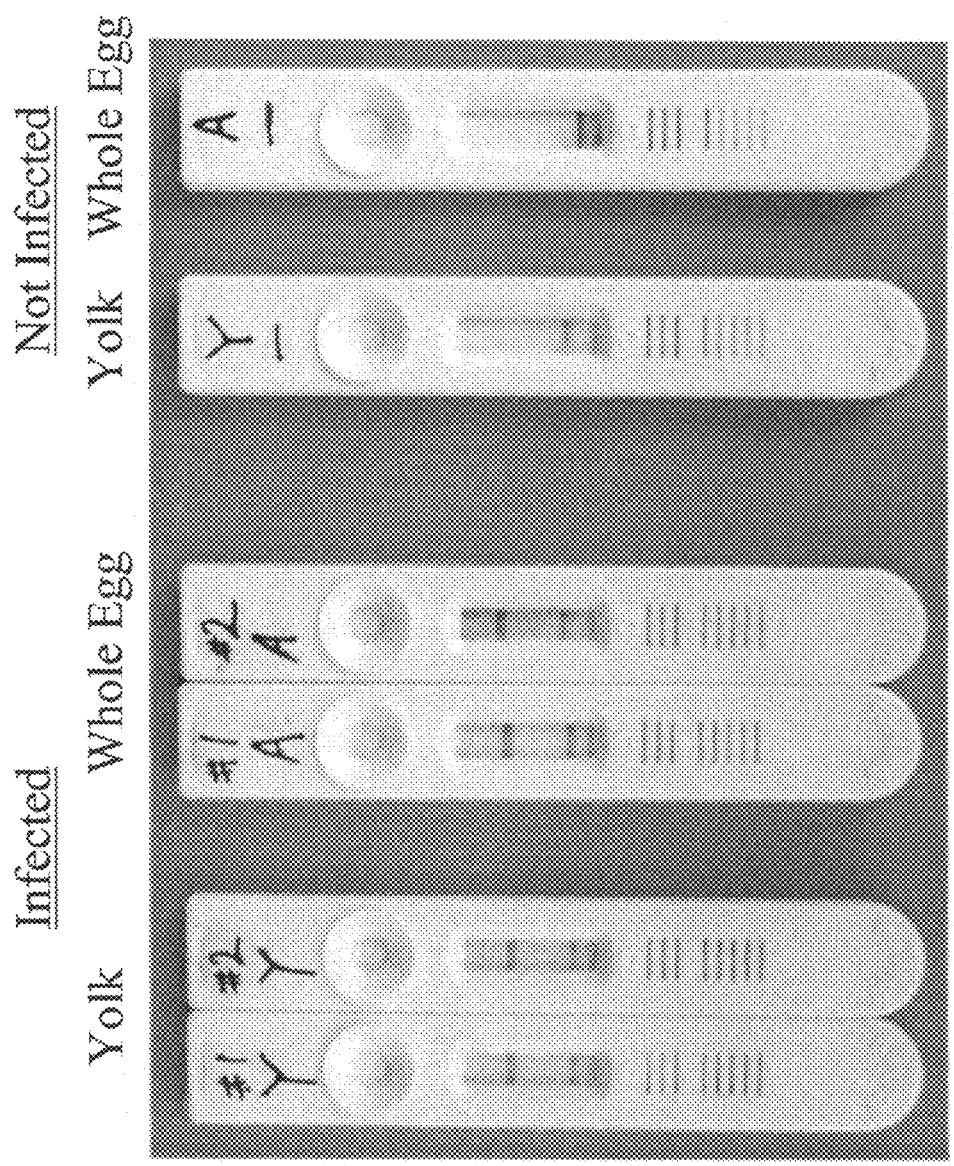
FIG. 4 is a photograph of lateral test panels showing detection of bacteria by yolk (Y) and whole egg contents (W).

Samples were prepared using fatty acid extraction for bacterial detection using a lateral panel as in example 2 with specific *Salmonella enteritidis* antibodies conjugated with gold particles. Eggs were contaminated as in Example 2. Egg yolk or whole egg contents were extracted as described above in Example 2 using oleic acid. Approximately 100 µl of the aqueous layer was removed and applied to the panel well. The reaction was complete within about one to two minutes (FIG. 4). No sensitivity is lost since there is no dilution of the sample as would occur if the albumin or yolk is diluted with saline and added directly to the test strip. Whole egg contents and albumin are more readily extracted than yolk.

Example 4

Fatty acids were tested for extraction efficiency of *Salmonella enteritidis* antibodies from whole eggs. Hens were infected by IV (about $10^7$ or about $10^5$ CFU in about a 0.5 ml dose in the wing vein) with SE as described in Example 1, experiment 2. Whole egg contents were prepared as in Example 1 and were directly, i.e. no dilution, mixed approximately 2:1 with caproic, caprylic, capric, oleic, or isostearic acid as described in Example 2, allowed to react until sample became viscous, approximately 1-2 minutes, and centrifuged for about 10 minutes at about 16,000×g. The clear aqueous layer was sampled, as described in example 1, for fluorescence polarization assay.

The results show that caprylic acid by itself is no different from the untreated immune control. Capric, oleic, and isostearic acids yielded nearly the same antibody titers at about 11 to about 16 points above the untreated immune control. Caproic acid did not yield a mean antibody titer above the nonimmune control.

TABLE 8

Homologous fluorescence polarization titers against *Salmonella enteritidis* from various fatty acid extractions of whole egg contents.

| Organic Acid | nonimmune control | Positive samples | | | | Cummulative pos. mean | Diff. over neg. control |
| --- | --- | --- | --- | --- | --- | --- | --- |
| | | 1 | 2 | 3 | 4 | | |
| no treatment supernatant | 95.8 | 163.1 | 146.8 | 193.4 | 193.9 | 174.3 | 78.5 |
| caproic (C6) | 94.8 | 86.9 | 94.1 | 97.8 | 96.8 | 93.9 | -0.9 |
| caprylic (C8) | 90.4 | 162.1 | 139.6 | 187.2 | 192.0 | 170.2 | 79.8 |
| capric (C10) | 94.1 | — | 158.5 | 207.8 | 200.6 | 189.0 | 95.0 |
| oleic (C18) | 92.7 | 171.4 | 153.4 | 206.0 | 197.3 | 182.0 | 89.3 |
| Isostearic (C18) | 91.5 | 172.4 | 150.3 | 206.4 | 200.6 | 182.4 | 90.9 |

The foregoing detailed description is for the purpose of illustration. Such detail is solely for that purpose and those skilled in the art can make variations without departing from the spirit and scope of the invention.

What is claimed is:

1. A method for extraction of a biological sample consisting essentially of:
    (a) adding at least one liquid carboxylic acid to a biological sample to form a first composition,
    (b) mixing said first composition to form a second composition that contains an aqueous soluble product,
    (c) centrifuging said second composition to form an aqueous layer and an oily layer, and
    (d) harvesting said aqueous layer to produce a concentrated sample selected from the group consisting of proteins, bacteria, virus, and mixtures thereof.

2. A method for obtaining purified antibodies from a biological sample consisting essentially of:
    (a) adding at least one liquid carboxylic acid to a sample to form a first composition,
    (b) mixing said first composition to form a second composition that contains an aqueous soluble product,
    (c) centrifuging said second composition to form an aqueous layer and an oily layer,
    (d) harvesting said aqueous layer to produce an extracted and concentrated antibody sample,
    (e) dialyzing said antibody sample, and
    (f) passing said dialysate over a chromatographic column to obtain a purified antibody preparation.

3. A method of extraction for a biological sample consisting essentially of:
    (a) adding at least one liquid carboxylic acid to a biological sample, to form a first composition,
    (b) mixing said first composition to form a second composition that contains an aqueous soluble product,
    (c) centrifuging said second composition to form an aqueous layer and an oily layer, and
    (d) harvesting said aqueous later which is a concentrated second sample selected from the group consisting of proteins, bacteria, virus, and mixtures thereof,
   wherein said aqueous layer which is a concentrated second sample is concentrated as compared to said biological sample.

4. The method of claim 3 wherein said at least one liquid carboxylic id is selected from the group consisting of caprylic acid, capric acid, oleic acid, isostearic acid, caproic acid, and mixtures thereof.

5. The method of claim 3 wherein said at least one liquid carboxylic acid is a mixture of two carboxylic acids.

6. The method of claim 5 wherein said mixture of two carboxylic acids selected from the group consisting of caprylic acid, capric acid, oleic acid, isostearic acid, and caproic acid.

7. A method for obtaining purified antibodies from a biological sample consisting essentially of:
    (a) adding at least one liquid carboxylic acid to an antibody containing biological sample to form a first composition,
    (b) mixing said first composition to form a second composition that contains an aqueous soluble product,
    (c) centrifuging said second composition to form an aqueous layer and an oily layer,
    (d) harvesting said aqueous layer which is an extracted and concentrated antibody containing second sample wherein said second sample is concentrated as compared to said antibody containing biological sample,
(e) dialyzing said antibody containing sample, and
(f) passing said dialysate over a chromatographic column to obtain a purified antibody preparation.

8. The method of claim 7 wherein said at least one liquid carboxylic acid is selected from the group consisting of caprylic acid, capric acid, oleic acid, isostearic acid, caproic acid, and mixtures thereof.

9. The method of claim 7 wherein said at least one liquid carboxylic acid is a mixture of two carboxylic acids.

10. The method of claim 9 wherein said mixture of two carboxylic acids is selected from the group consisting of caprylic acid, capric acid, oleic acid, isostearic acid, and caproic acid.

* * * * *